(12) United States Patent
Raduti

(10) Patent No.: US 10,525,069 B2
(45) Date of Patent: Jan. 7, 2020

(54) TREATMENT OF URINARY TRACT INFECTION

(71) Applicant: BIOMEDICALS SWEDEN AB, Kallered (SE)

(72) Inventor: Constantin Raduti, Kallered (SE)

(73) Assignee: BIOMEDICALS SWEDEN AB, Kallered (SE)

( * ) Notice: Subject to any disclaimer, the term of this patent is extended or adjusted under 35 U.S.C. 154(b) by 0 days.

(21) Appl. No.: 15/321,902

(22) PCT Filed: Jun. 29, 2015

(86) PCT No.: PCT/SE2015/050757
§ 371 (c)(1),
(2) Date: Dec. 23, 2016

(87) PCT Pub. No.: WO2016/003358
PCT Pub. Date: Jan. 7, 2016

(65) Prior Publication Data
US 2017/0173058 A1    Jun. 22, 2017

(30) Foreign Application Priority Data
Jul. 2, 2014 (SE) ...................................... 1450829

(51) Int. Cl.
| | | |
|---|---|---|
| A61K 31/7004 | (2006.01) |
| A61K 31/194 | (2006.01) |
| A61K 33/10 | (2006.01) |
| A61K 31/19 | (2006.01) |
| A61K 9/20 | (2006.01) |

(52) U.S. Cl.
CPC ............ *A61K 31/7004* (2013.01); *A61K 9/20* (2013.01); *A61K 31/19* (2013.01); *A61K 31/194* (2013.01); *A61K 33/10* (2013.01)

(58) Field of Classification Search
CPC .. A61K 31/19; A61K 31/194; A61K 31/7004; A61K 33/10; A61K 9/20; A61K 45/06; A61K 2300/00; Y02A 50/473
See application file for complete search history.

(56) References Cited

U.S. PATENT DOCUMENTS

2009/0175843 A1* 7/2009 Gans .................... A61K 31/375
424/94.65

FOREIGN PATENT DOCUMENTS

| EP | 2535047 | 12/2012 |
| WO | WO 2009/089442 | 7/2009 |
| WO | WO 2011/073112 | 6/2011 |

OTHER PUBLICATIONS

Erdogan-Yildririm, Z, "Impact of pH on bacterial growth and actvity of recent fluoroquinolones in pooled urine", *Research in Microbiology* 162(3): 249-252 (2011).
European Search Report corresponding to International Application No. PCT/SE2015/050757; dated Sep. 29, 2015, 5 pages.
Padan E et al. Alkaline pH homeostasis in bacteria: new insights. Biochim Biophys Acta. Nov. 2005: 1717(2): 67-88.
Maurer LM et al. pH regulates genes for flagellar motility, catabolism, and oxidative stress in *Escherichia coli* K-12. Journal of Bacteriology. Jan. 2005; 187(1): 304-319.
Schuldiner S et al. Induction of SOS functions by alkaline intracellular pH in *Eschericia coli*. Journal of Bacteriology, Nov. 1986; 168(2): 936-939.
Rimon A et al. A point mutation (G338S) and its suppressor mutations affect both the pH response of the NhaA-Na+/H+ antiporter as well as the growth phenotype of *Escherida coli*. Journal of Biological Chemistry. Oct. 1998; 273(41): 26470-26476.

* cited by examiner

*Primary Examiner* — Snigdha Maewall
(74) *Attorney, Agent, or Firm* — Myers Bigel, P.A.

(57) ABSTRACT

The embodiments relate to compositions useful in the treatment, inhibition or prevention of urinary tract infection in a subject. The compositions comprise a pH increasing agent, a pH decreasing agent and man nose or an analogue thereof. The pH increasing agent and the pH decreasing agent are provided to be alternately administered to the subject.

19 Claims, No Drawings

TREATMENT OF URINARY TRACT INFECTION

STATEMENT OF PRIORITY

This application is a 35 U.S.C. § 371 national phase application of International Application Serial No. PCT/SE2015/050757, filed Jun. 29, 2015, which claims the benefit, under 35 U.S.C. § 119 (a) of Swedish Patent Application No. 1450829-5, filed Jul. 2, 2014, the entire contents of each of which are incorporated by reference herein.

TECHNICAL FIELD

The present embodiments generally relate to treatment, inhibition or prevention of urinary tract infection in a subject, and in particular to treatment, inhibition or prevention of urinary tract infection by alternating increasing and decreasing pH in the urinary tract of the subject in combination with mannose administration.

BACKGROUND

Urinary tract infection (UTI), sometimes also referred to as acute cystitis or bladder infection, is an infection that affects part of the urinary tract. UTI is usually caused by bacteria entering the urinary tract via the urethra. The bacteria can then move upwards through the urinary tract, infecting the bladder (a condition known as cystitis) and sometimes the kidneys (a condition called pyelonephritis). Symptoms of a lower UTI include pain or a burning sensation when passing urine (called dysuria) and/or the feeling of not being able to urinate fully. The patient may also suffer from cloudy, bloody or bad-smelling urine. Lower abdominal pain, mild fever, delirium or acute confusion may also occur.

It is particularly common for older people living in care homes to have bacteria in their urine because their flow of urine is weaker and they are less likely to empty their bladder fully. Urinary tract disorders, such as an enlarged prostate in men or a prolapse in women, may cause bladder emptying problems that may contribute to UTI. Urinary catheters are a common cause of UTI. UTI is the most common hospital acquired infection, accounting for about 23% of all infections, and the majority of these are associated with catheters.

Recurrences are common and if a person has more than two episodes of UTI in three months, this is described as recurrent UTI.

The main causal agent of UTI is *Escherichia coli*, though other bacteria, viruses or fungi may rarely be the cause.

Traditionally, UTI is treated by antibiotics, although resistance to antibiotics is an increasing problem with regard to UTI. In complicated cases, longer course or intravenous antibiotics may be needed, and if symptoms have not improved in two or three days, further diagnostic testing is needed.

Administration of antibiotics to patients suffering from UTI is not without problems. Firstly, more and more UTI-causing bacterial strains show resistance to the antibiotics traditionally used when treating UTI as mentioned above. Secondly, the antibiotics do not only affect the UTI-causing bacteria but also have side effects in terms of negatively affecting the normal body micro flora.

WO 2009/089442 discloses the usage of a human dietary supplement composition comprising a cranberry derivative or proanthocyanidin-containing concentrate and D-mannose for preventing, controlling and ameliorating UTI caused by *E. coli*. WO 2011/073112 discloses mannose derivatives useful for the prevention and treatment of bacterial infections, in particular of urinary infections caused by *E. coli*.

*Research in Microbiology* 2011, 162(3): 249-252 investigates the effect of modification of pH on bacterial growth of *E. coli* ATCC 25922 and *Klebsiella oxytoca* ATCC 700324 as well as on activity of modern fluoroquinolones in urine in vitro. There was no difference in bacterial growth of *E. coli* and *K. oxytoca* observed at pH values between 5.0 and 8.0. However, acidification of urine led to a major impairment of the antimicrobial activity of the tested fluoroquinolones. It was postulated that the reduction in pH impaired uptake of fluoroquinolones into the bacterial cells.

There is still need for an efficient treatment for UTI that is not marred by the problems and shortcomings of traditional antibiotics-based treatment regimens.

SUMMARY

It is a general objective to provide an efficient treatment for UTI.

This and other objectives are met by embodiments as disclosed herein.

Briefly, an aspect of the embodiments relates to a composition comprising a pH increasing agent, a pH decreasing agent and mannose or an analogue thereof for use in treatment, inhibition or prevention of urinary tract infection in a subject, wherein an administration pattern of the composition comprises alternately administering the pH increasing agent and the pH decreasing agent to the subject and administering the mannose or the analogue thereof to the subject.

Another aspect of the embodiments relates to use of a composition comprising a pH increasing agent, a pH decreasing agent and mannose or an analogue thereof for the manufacture of a medicament for treatment, inhibition or prevention of urinary tract infection in a subject, wherein an administration pattern of the composition comprises alternately administering the pH increasing agent and the pH decreasing agent to the subject and administering the mannose or the analogue thereof to the subject.

A further aspect of the embodiments relates to a method for treatment, inhibition or prevention of urinary tract infection in a subject. The method comprises alternately administering a pH increasing agent in combination with mannose or an analogue thereof and a pH decreasing agent in combination with the mannose or the analogue thereof to the subject.

Yet another aspect of the embodiments relates to a method of inducing loss of antibiotic resistance in an antibiotic-resistant bacterial strain. The method comprising alternating exposing the antibiotic-resistant bacterial strain to a basic pH and an acidic pH.

A further aspect of the embodiments relates to a composition comprising a pH increasing agent and a pH decreasing agent for use in inducing loss of antibiotic resistance in an antibiotic-resistant bacterial strain having infected a subject, wherein an administration pattern of the composition comprises alternately administering the pH increasing agent and the pH decreasing agent to the subject.

The present embodiments achieve an efficient treatment, inhibition or prevention of UTI in subjects without the shortcomings of traditional antibiotics-based treatment regimens. Thus, the present embodiments do not contribute towards multi-resistant bacteria and do not negatively affect the micro flora in the gastrointestinal tract.

DETAILED DESCRIPTION

The present embodiments generally relate to treatment or prevention of urinary tract infection (UTI) in a subject, and in particular to treatment or prevention of UTI by using mannose as anti-adhesion agent in combination with increasing and decreasing pH in the urinary tract system of a subject suffering from UTI.

Cranberry comprising the sugar mannose has traditionally been employed for treatment of UTI since mannose seems to prevent UTI-causing bacteria from attaching and binding to the walls of the urinary tract and bladder. Mannose binds to lectin molecules on the cell walls of UTI-causing bacteria, and in particular *Escherichia coli*, thereby preventing the lectin molecules from attaching the *E. coli* bacteria to carbohydrate molecules in the walls of the urinary tract system. This anti-adhesion effect of mannose causes the *E. coli* bacteria to be flushed away from the urinary tract system.

The present invention is based on the unexpected discovery that the effect of mannose and analogues thereof with regard to UTI can be significantly improved by exposing the UTI-causing bacteria to a stress to inhibit cell growth. This inhibition of cell growth is, according to the embodiments, achieved by exposing the UTI-causing bacteria to changes in pH in the urinary tract system in connection with mannose administration. In particular, the embodiments provide alternate increases and decreases in pH in the urinary tract system in connection with mannose administration to achieve treatment, inhibition and/or prevention of UTI in a subject, preferably a mammalian subject, and more preferably a human subject.

Urinary tract system as used herein encompasses the urinary bladder (vesica urinaria) and the urinary tract (urethra). The urinary tract system is part of the urinary or renal system additionally comprising the kidneys (ren) and the ureters. UTI may occur in the urinary tract, the urinary bladder or indeed also the ureters and kidneys. Thus, UTI-bacteria may be present not only in the urinary tract system but indeed in all or at least some of the tissues or organs of the renal system.

Hence, an aspect of the embodiments relates to a composition comprising a pH increasing agent, a pH decreasing agent and mannose or an analogue thereof for use in treatment, inhibition or prevention of UTI in a subject, wherein an administration pattern of the composition comprises alternately administering the pH increasing agent and the pH decreasing agent to the subject and administering the mannose or the analogue thereof to the subject.

The components of the composition can be provided as separate ingredients, i.e. the pH increasing agent, the pH decreasing agent and the mannose or the analogue thereof. Alternatively, the mannose or the analogue thereof can be mixed with the pH increasing agent and/or the pH decreasing agent, preferably with both the pH increasing agent and the pH decreasing agent. In such a case, the composition comprises first dosage units comprising the pH increasing agent and the mannose or the analogue thereof, preferably in the form of a mixture of the pH increasing agent and the mannose or the analogue thereof. The composition also comprises second dosage units comprising the pH decreasing agent and the mannose or the analogue thereof, preferably in the form of a mixture of the pH decreasing agent and the mannose or the analogue thereof.

In the former case, i.e. separate ingredients, the pH increasing agent and the pH decreasing agent can be administered separately from administration of the mannose or the analogue thereof. Alternatively, the pH increasing agent could be administered substantially at the same time as the mannose or the analogue thereof and/or, preferably and, the pH decreasing agent could be administered substantially at the same time as the mannose or the analogue thereof.

In a preferred embodiment, an administration pattern or protocol of the composition comprises alternately administering the pH increasing agent and the pH decreasing agent to the subject and administering the mannose or the analogue thereof to the subject.

The alternate administration of the pH increasing agent and the pH decreasing agent causes a change or switch in pH in the urinary tract system, which in turn stresses any bacteria present therein. The pH-induced stress will inhibit or at least reduce the growth rate of the bacteria, thereby potentiating the anti-adhesion effect of the mannose or the analogue thereof.

Changing pH by the composition of the embodiments in the urinary tract system encompasses changing pH in the urinary tract of the subject, changing pH in the urinary bladder of the subject or changing pH in the urinary tract and bladder of the subject.

The administration pattern preferably specifies that the pH increasing agent is administered to the subject at every second administration occasion and that the pH decreasing agent is administered to the subject at the other administration occasions. For instance, the pH increasing agent could be administered at the $1^{st}$, $3^{rd}$, $5^{th}$, etc. administration occasion (odd numbered administration occasions) and the pH decreasing agent is administered at the $2^{nd}$, $4^{th}$, $6^{th}$, etc. administration occasion (even numbered administration occasions. Also the opposite case is possible with administration of the pH increasing agent at the even numbered administration occasions and administration of the pH decreasing agent at the odd numbered administration occasions.

Although it is generally preferred to switch between the pH increasing agent and the pH decreasing agent at every administration occasion, the embodiments are not limited thereto. For instance, the pH increasing agent (or the pH decreasing agent) could be administered to the subject at the first N administration occasions, followed by administering the pH decreasing agent (or the pH increasing agent) at the following M administration occasions, followed by N administration occasions of the pH increasing agent (or the pH decreasing agent), and so on. In an embodiment, N, M are positive numbers equal to or larger than one, preferably N, M$\in[1, 3]$, more preferably N, M=1 or 2, such as N=M=1. In an embodiment, M is preferably equal to N.

For instance, one of the pH increasing agent and pH decreasing agent could be administered to the subject at the first two administration occasions, followed by administering the other of the pH increasing agent and the pH decreasing agent at the following administration occasion or the following two administration occasions. This corresponds to administration of one of the agents at the $1^{st}$, $2^{nd}$, $4^{th}$, $5^{th}$, $7^{th}$, $8^{th}$, and so on, or $1^{st}$, $2^{nd}$, $5^{th}$, $6^{th}$, $9^{th}$, $10^{th}$, and so on, administration occasions and the other agent at the $3^{rd}$, $6^{th}$, $9^{th}$, and so on, or $3^{rd}$, $4^{th}$, $7^{th}$, $8^{th}$, $11^{th}$, $12^{th}$, and so on, administration occasions.

The values of the parameters N, M typically depend on the frequency of the administration occasions. In an embodiment, the values of the parameters N, M are preferably smaller for a low frequency of administration occasion, i.e.

long time between two administration occasions, as compared to a high frequency of administration, i.e. shorter time between two administration occasions.

The pH increasing agent is preferably a base and the pH decreasing agent is preferably an acid. The pH increasing agent thereby preferably has a pH value higher than 7 in an aqueous solution and the pH decreasing agent preferably has a pH value lower than 7 in an aqueous solution.

The pH value in the urinary tract system is preferably changing between a more basic pH value and a more acidic pH value with regard to the baseline or normal pH level in the urinary tract system when administrating the pH increasing agent and the pH decreasing agent and if not countered by any buffering action. This change between more basic and acidic pH values induces the growth-inhibiting effect to any UTI-causing bacteria that may be present in the urinary tract system.

Administration of the mannose or the analogue thereof can be made independent of the administrations of the pH increasing agent and the pH decreasing agent. For instance, the mannose or the analogue thereof could be administered in between the administration occasions for the pH increasing and decreasing agents.

However, it is generally preferred to co-administer the mannose or the analogue thereof and the pH increasing agent or the pH decreasing agent or administer the mannose or the analogue thereof at least substantially at the same time as administering the pH increasing agent or the pH decreasing agent. In such a case, the mannose or the analogue thereof and the pH increasing agent could be administered as two separate dosage units taken at substantially the same time and the mannose or the analogue thereof and the pH decreasing agent could be administered as two separate dosage units taken at substantially the same time.

In an embodiment, the composition comprises a pH increasing part composition comprising the pH increasing agent and the mannose or the analogue thereof and a pH decreasing part composition comprising the pH decreasing agent and the mannose or the analogue thereof. In such a case, the administration pattern preferably comprises alternately administering the pH increasing part composition and the pH decreasing part composition to the subject.

The alternate administration of the pH increasing part composition and the pH decreasing part composition to the subject preferably induces an alternation of the pH value in the urinary tract system of the subject.

The pH increasing part composition comprises the pH increasing agent and the mannose or the analogue thereof as separate dosage units that are, however, co-administered or at least administered substantially at the same time to the subject. Correspondingly, the pH decreasing part composition comprises the pH decreasing agent and the mannose or the analogue thereof as separate dosage units that are co-administered or at least administered substantially at the same time to the subject.

In another embodiment, the composition comprises first dosage units comprising the pH increasing part composition, such as in the form of a mixture of the pH increasing agent and the mannose or the analogue thereof. The composition also comprises second dosage units comprising the pH decreasing part composition, such as in the form of a mixture of the pH decreasing agent and the mannose or the analogue thereof. This means that administration of a first/second dosage unit implies that both mannose or the analogue and the pH increasing/decreasing agent will be co-administered, preferably as a mixture, to the subject.

Each first dosage unit preferably comprises 0.1 to 4 g of the pH increasing agent and 0.5 to 10 g of the mannose or the analogue thereof. Correspondingly, each second dosage unit preferably comprises 0.1 to 4 g of the pH decreasing agent and 0.5 to 10 g of the mannose or the analogue thereof.

In an embodiment, each first dosage unit preferably comprises 0.1 to 4 g, preferably 0.25 to 4 g, such as 0.5 to 4 g, more preferably 0.5 to 2 g, such as 0.5 to 1.5 g, and in particular 1 g of the pH increasing agent and 0.5 to 5 g, such as 0.5 to 4 g or 1 to 5 g, preferably 1.5 to 5 g, more preferably 1.5 to 3.5 g, and in particular 2 g or 3 g of the mannose or the analogue thereof. Correspondingly, each second dosage unit preferably comprises 0.1 to 4 g, preferably 0.25 to 4 g, such as 0.5 to 4 g, more preferably 0.5 to 2 g, such as 0.5 to 1.5 g, and in particular 1 g of the pH decreasing agent and 0.5 to 5 g, such as 0.5 to 4 g or 1 to 5 g, preferably 1.5 to 5 g, more preferably 1.5 to 3.5 g, and in particular 2 g or 3 g of the mannose or the analogue thereof.

In a particular example, each first dosage unit preferably comprises about 0.5 g or 1 g of the pH increasing agent and about 2 g or 3 g of the mannose or the analogue thereof. Correspondingly, each second dosage unit preferably comprises about 0.5 g or 1 g of the pH decreasing agent and about 2 g or 3 g of the mannose or the analogue thereof.

In an example, the each first dosage unit comprises about 1 g of the pH increasing agent and about 2 g of the mannose or the analogue thereof and each second dosage comprises about 1 g of the pH decreasing agent and about 2 g of the mannose or the analogue thereof. In this example, the dosage units are preferably administered 5 times a day, such as for 5 days.

In another example, the each first dosage unit comprises about 1 g of the pH increasing agent and about 3 g of the mannose or the analogue thereof and each second dosage comprises about 1 g of the pH decreasing agent and about 3 g of the mannose or the analogue thereof. In this example, the dosage units are preferably administered 3 times a day, such as for 5 days.

The first and second dosage units may be provided in various administration formulas or forms suitable for oral administration, intravenous administration or subcutaneous administration, preferably oral administration.

In particular for oral administration, the first and second dosage units may be powder mixtures to be dissolved in water or another drinkable liquid, tablets, pills, lozenges, capsules, drops, liquid syrups, oral sprays, gels, etc.

The first and second dosage units may comprise the active ingredients alone or the active ingredients and at least one excipient. For instance, if the first and second dosage units are provided as powder mixtures silica can be added as an excipient to prevent the powder from aggregating or compacting upon exposure to moisture.

Non-limiting examples of excipients that can be used according to the embodiments include anti-adherents, binders, coatings, disintegrants, filers, flavours, colors, lubricants, glidants, sorbents, preservatives and sweeteners.

An example of dosage units that can be used for oral administration is to provide the first dosage units as sachets comprising the pH increasing part composition as a powder mixture of the pH increasing agent and the mannose or the analogue thereof and the second dosage units as sachets comprising the pH decreasing part composition as a powder mixture of the pH decreasing agent and the mannose or the analogue thereof.

The sachets are then opened prior to administration and the powder mixture present therein is preferably added to water or another drinkable liquid to form a solution or a suspension.

Another example of dosage units that can be used for oral administration is to provide the first dosage units as tablets or lozenges comprising the pH increasing part composition as a mixture of the pH increasing agent and the mannose or the analogue thereof and the second dosage units as tablets or lozenges comprising the pH decreasing part composition as a mixture of the pH decreasing agent and the mannose or the analogue thereof.

In an embodiment, the sachets, tablets or lozenges may have a respective number specifying an administration order according to the administration pattern. For instance, the sachets, tablets or lozenges may be numbered 1, 2, 3, and so forth to inform the subject that the sachet, tablet or lozenge number 1 should be taken at the first administration occasion, the sachet, tablet or lozenge number 2 should be taken at the second administration occasion, and so on.

In such a case, it is not necessary for the subject to mind which sachets, tablets or lozenges that comprise the pH increasing part composition and which sachets, tablets or lozenges that comprise the pH decreasing part composition. Hence, the subject merely has to make sure that the sachets, tablets or lozenges are taken according to the administration order specified by the respective numbers.

Numbering dosage units can of course be applied to other dosage forms than sachets with powder mixtures, tablets and lozenges.

Alternatively, or in addition, different colors or patterns can be used to simplify discriminating the first dosage units from the second dosage units. For instance, the first dosage units may have a first color or pattern and the second dosage units may have a second color or pattern that is different from the first color or pattern.

This coloring can be achieved by adding colors to the pH increasing and decreasing part compositions. Alternatively, or in addition, the package units, such as sachets, blister packets, etc. containing the pH and increasing and decreasing part compositions may be colored or patterned differently to simplify telling the first and second dosage units apart.

I.v. and s.c. formulations could be in the form of injection solutions, such as water, saline or buffered aqueous injection solutions in which the pH increasing part compositions and the pH decreasing part compositions are dissolved.

In an embodiment, the administration pattern comprises administering a part composition to the subject 3 to 7 times a day. In a preferred embodiment, every second administered part composition is a pH increasing part composition and the other administered part compositions are a respective pH decreasing part composition.

In a particular embodiment, the administration pattern comprises administering a part composition to the subject 3 times or 5 times a day. In a preferred embodiment, every second administered part composition is a pH increasing part composition and the other administered part compositions are a respective pH decreasing part composition.

In an embodiment, the administration pattern comprises administering a part composition to the subject 3 to 7 times a day during 2 to 10 days. In a preferred embodiment, every second administered part composition is a pH increasing part composition and the other administered part compositions are a respective pH decreasing part composition.

In an embodiment, the administration pattern comprises administering a part composition to the subject 3 times or 5 times a day during 2 to 10 days. In a preferred embodiment, every second administered part composition is a pH increasing part composition and the other administered part compositions are a respective pH decreasing part composition.

For instance, the administration pattern comprises administering a part composition to the subject three or five times a day during four, five, six or seven days.

For continuous or long-term administration, such as in the case of preventing UTI, a fewer number of administration occasions may be used as compared to transient administration, such as in the case of treating a subject suffering from UTI. For instance, if about three to five administrations are used per day in the administration pattern for treatment application then about three or fewer administrations could be used per day in the administration pattern for preventive application.

The pH increasing agent is preferably administered to the subject at a dosage of 0.1 to 20 g per day, the pH decreasing agent is preferably administered to the subject at a dosage of 0.1 to 20 g per day and the mannose or the analogue thereof is preferably administered at a dosage of 0.1 to 50 g per day.

In a particular embodiment, the pH increasing agent is preferably administered to the subject at a dosage of 1 to 3 g per day, such as 1 to 2 g per day or 1 to 1.5 g per day, the pH decreasing agent is preferably administered to the subject at a dosage of 1 to 3 g per day, such as 1 to 2 g per day or 1 to 1.5 g per day and the mannose or the analogue thereof is preferably administered at a dosage of 5 to 15 g, preferably 6 to 15 or 6 to 10 g per day, such as about 10 g or 15 g per day.

The pH increasing agent is preferably selected from a group consisting of a carbonate, a lactate, a hydroxide, an amine, an amide, an ammonium salt, ammonium, alanine and pyridine.

The carbonate is preferably selected from a group consisting of sodium bicarbonate, sodium carbonate, potassium bicarbonate, potassium carbonate, magnesium carbonate and calcium carbonate, or a mixture thereof. In a preferred embodiment, the carbonate is calcium carbonate.

The lactate is preferably selected from a group consisting of sodium lactate, potassium lactate and calcium lactate, or a mixture thereof. In a preferred embodiment, the lactate is potassium lactate.

The hydroxide is preferably selected from a group consisting of sodium hydroxide, potassium hydroxide, barium hydroxide, ammonium hydroxide, calcium hydroxide, lithium hydroxide, magnesium hydroxide and beryllium hydroxide, or a mixture thereof.

The amine is preferably methylamine, the amide is preferably acetazolamide and the ammonium salt is preferably ammonium chloride.

In an embodiment, the pH increasing agent is calcium carbonate or potassium lactate.

The pH decreasing agent is preferably selected from a group consisting of citric acid, a straight-chain, saturated carboxylic acid, lactic acid, ascorbic acid, tartaric acid, mandelic acid, acetylsalicylic acid, benzoic acid, boric acid, ethylenediaminetetaacetic acid (EDTA), carbonic acid, maleic acid, hydrochloride, hypochlorous acid, a hypochlorite, such as sodium hypochlorite, potassium chlorite or calcium hypochlorite.

The straight-chain, saturated carboxylic acid is preferably selected from a group consisting of fumaric acid, acetic acid, propionic acid, butyric acid and valeric acid, or a mixture thereof.

In an embodiment, the pH decreasing agent is lactic acid or citric acid.

The mannose ($C_6H_{12}O_6$) can be in in a diastereomer form, i.e. D-mannose or L-mannose, or be in the form of a mixture of D-mannose and L-mannose, such as a racemate of D-mannose and L-mannose.

Mannose commonly exists as two different sized rings, the pyranose (six-membered) form and the furanose (five-membered) form. Each ring closure can have either an alpha or beta configuration at the anomeric position. The chemical rapidly undergoes isomerization among these four forms.

The D-mannose can therefore be in the form of α-D-mannopyranose, β-D-mannopyranose, α-D-mannofuranose, β-D-mannofuranose, a mixture of the pyranoses, a mixture of the furanoses, a mixture of at least one pyranose and at least one furanose, or a mixture of the pyranoses and the furanoses. Generally, D-mannose is in the form of a mixture of about 67% α-D-mannopyranose, 33% β-D-mannopyranose, <1% α-D-mannofuranose and <1% β-D-mannofuranose.

The L-mannose can be in the form of α-L-mannopyranose, β-L-mannopyranose, α-L-mannofuranose, β-L-mannofuranose, a mixture of the pyranoses, a mixture of the furanoses, a mixture of at least one pyranose and at least one furanose, or a mixture of the pyranoses and the furanoses.

Mannose is sometimes also referred to as semonose or carubinose.

The mannose is preferably in the form of D-mannose.

A preferred analogue of mannose is mannitol ($C_6H_{14}O_6$). Mannitol is classified as a sugar alcohol that is derived from mannose by reduction. Other analogues of mannose that can be used according to the embodiments are disclosed in WO 2011/073112 and defined by formula (I)

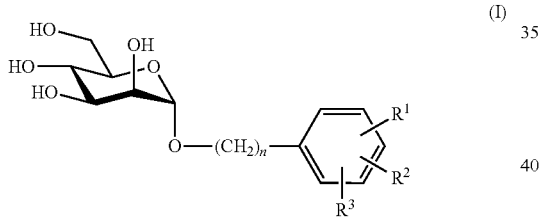

wherein n is 0, 1 or 2;

$R^1$ is phenyl connected to the phenyl ring of formula (I) in meta- or para-position and substituted by one, two or three substituents selected from the group consisting of lower alkyl, halo-lower alkyl, hydroxy-lower alkyl, lower alkoxy-lower alkyl, optionally substituted alkenyl, optionally substituted alkinyl, cyclohexyl, cyclopropyl, aryl, heteroaryl, heterocyclyl; para-hydroxy, lower alkoxy, halo-lower alkoxy, lower alkoxy-lower alkoxy, cycloalkyloxy, hydroxysulfonyloxy; mercapto, alkylmercapto, hydroxysulfinyl, alkylsulfinyl, halo-lower alkylsulfinyl, hydroxysulfonyl, alkylsulfonyl, arylsulfonyl, heteroarylsulfonyl, aminosulfonyl wherein amino is unsubstituted or substituted by one or two substitutents selected from lower alkyl, cycloalkyl-lower alkyl, hydroxy-lower alkyl, lower alkoxy-lower alkyl, optionally substituted phenyl-lower alkyl and optionally substituted heteroaryl-lower alkyl, or wherein the two substituents on nitrogen form together with the nitrogen heterocyclyl; amino optionally substituted by one or two substitutents selected from lower alkyl, cycloalkyl-lower alkyl, hydroxy-lower alkyl, lower alkoxy-lower alkyl and di-lower alkylamino-lower alkyl, or by one substituent cycloalkyl, optionally substituted phenyl, optionally substituted heteroaryl, alkylcarbonyl, optionally substituted phenylcarbonyl, optionally substituted pyridylcarbonyl, alkoxycarbonyl or aminocarbonyl, or wherein the two substituents on nitrogen form together with the nitrogen heterocyclyl; carboxymethylamino or lower alkoxycarbonylmethylamino substituted at the methyl group such that the resulting substituent corresponds to one of the 20 naturally occurring standard amino acids, aminomethylcarbonylamino substituted at the methyl group such that the resulting acyl group corresponds to one of the 20 naturally occurring standard amino acids; lower alkylcarbonyl, halo-lower alkylcarbonyl, para-carboxy, lower alkoxycarbonyl, lower alkoxy-lower alkoxycarbonyl; aminocarbonyl wherein amino is unsubstituted or substituted by one hydroxy or amino group or one or two substitutents selected from lower alkyl, hydroxy-lower alkyl, lower alkoxy-lower alkyl, optionally substituted phenyl-lower alkyl and optionally substituted heteroaryl-lower alkyl, or wherein the two substituents on nitrogen form together with the nitrogen heterocyclyl; cyano, halogen, and nitro; and wherein two substituents in ortho-position to each other can form a 5- or 6-membered heterocyclic ring containing one or two oxygen atoms and/or one or two nitrogen atoms, wherein the nitrogen atoms are optionally substituted by lower alkyl, lower alkoxy-lower alkyl or lower alkylcarbonyl; or $R^1$ is aryl other than optionally substituted phenyl, heteroaryl, heterocyclyl with 5 or more atoms, optionally substituted phenylamino, or optionally substituted phenyl-thioureido; and $R^2$ and $R^3$ are, independent of each other, hydrogen, lower alkyl, halo-lower alkyl, hydroxy-lower alkyl, lower alkoxy-lower alkyl, optionally substituted alkenyl, optionally substituted alkinyl, cycloalkyl, hydroxy, lower alkoxy, halo-lower alkoxy, lower alkoxy-lower alkoxy, phenoxy, hydroxysulfonyloxy; mercapto, alkylmercapto, hydroxysulfinyl, alkyl-sulfinyl, halo-lower alkylsulfinyl, hydroxysulfonyl, alkylsulfonyl, arylsulfonyl, heteroaryl-sulfonyl, aminosulfonyl, amino optionally substituted by one or two substituents selected from lower alkyl, hydroxy-lower alkyl, lower alkoxy-lower alkyl; lower alkylcarbonylamino, alkoxycarbonylamino, benzoylamino, pyridinylcarbonylamino, carboxymethylamino or lower alkoxycarbonylmethylamino substituted at the methyl group such that the resulting substituent corresponds to one of the 20 naturally occurring standard amino acids, aminomethylcarbonylamino substituted at the methyl group such that the resulting acyl group corresponds to one of the 20 naturally occurring standard amino acids; carboxy, lower alkylcarbonyl, benzoyl, pyridinecarbonyl, pyrimidinecarbonyl, lower alkoxycarbonyl, aminocarbonyl, wherein amino is unsubstituted or substituted by one hydroxy or amino group or one or two substitutents selected from lower alkyl, hydroxy-lower alkyl or lower alkoxy-lower alkyl; tetrazolyl, cyano, halogen, or nitro; or wherein two substituents in ortho-position to each other form a 5- or 6-membered heterocyclic ring containing one or two oxygen atoms and/or one or two nitrogen atoms, wherein the nitrogen atoms are optionally substituted by lower alkyl, lower alkoxy-lower alkyl or lower alkylcarbonyl.

In a particular embodiment, the composition comprises calcium carbonate, lactic acid and the mannose or the analogue thereof, preferably D-mannose.

In another particular embodiment, the composition comprises potassium lactate, lactic acid and the mannose or the analogue thereof, preferably D-mannose.

In a further particular embodiment, the composition comprises calcium carbonate, citric acid and mannose or the analogue thereof, preferably D-mannose.

In yet another particular embodiment, the composition comprises potassium lactate, citric acid and mannose or the analogue thereof, preferably D-mannose.

In an embodiment, 0.5 g calcium carbonate and 2 g D-mannose are mixed to form a respective first dosage unit. 0.5 g lactic acid and 2 g D-mannose are mixed to form a respective second dosage unit. Alternatively, 1 g calcium carbonate and 2 g D-mannose are mixed to form a respective first dosage unit and 1 g lactic acid and 2 g D-mannose are mixed to form a respective second dosage unit, or 1 g calcium carbonate and 3 g D-mannose are mixed to form a respective first dosage unit and 1 g lactic acid and 3 g D-mannose are mixed to form a respective second dosage unit.

In another embodiment, 0.5 g calcium carbonate and 2 g D-mannose are mixed to form a respective first dosage unit. 0.5 g citric acid and 2 g D-mannose are mixed to form a respective second dosage unit. Alternatively, 1 g calcium carbonate and 2 g D-mannose are mixed to form a respective first dosage unit and 1 g citric acid and 2 g D-mannose are mixed to form a respective second dosage unit, or 1 g calcium carbonate and 3 g D-mannose are mixed to form a respective first dosage unit and 1 g citric acid and 3 g D-mannose are mixed to form a respective second dosage unit.

In a further embodiment, 0.5 g potassium lactate and 2 g D-mannose are mixed to form a respective first dosage unit. 0.5 g lactic acid and 2 g D-mannose are mixed to form a respective second dosage unit. Alternatively, 1 g potassium lactate and 2 g D-mannose are mixed to form a respective first dosage unit and 1 g lactic acid and 2 g D-mannose are mixed to form a respective second dosage unit, or 1 g potassium lactate and 3 g D-mannose are mixed to form a respective first dosage unit and 1 g lactic acid and 3 g D-mannose are mixed to form a respective second dosage unit.

In yet another embodiment, 0.5 g potassium lactate and 2 g D-mannose are mixed to form a respective first dosage unit. 0.5 g citric acid and 2 g D-mannose are mixed to form a respective second dosage unit. Alternatively, 1 g potassium lactate and 2 g D-mannose are mixed to form a respective first dosage unit and 1 g citric acid and 2 g D-mannose are mixed to form a respective second dosage unit, or 1 g potassium lactate and 3 g D-mannose are mixed to form a respective first dosage unit and 1 g citric acid and 3 g D-mannose are mixed to form a respective second dosage unit.

In an embodiment, the first and second dosage units according to any of the above mentioned embodiments is alternative administered to the subject during four to seven days, for a total of three or five times per day.

It is also possible to have an administration protocol with different number of dosage units for different treatment periods, see for instance, Table 2 and 3. For instance, the first and second dosage units according to any of the above mentioned embodiments could be alternative administered to the subject during four to seven days, for a total of five times per day. Thereafter, the first and second dosage units according to any of the above mentioned embodiments could be alternative administered to the subject for a total of three times per day. This latter administration with three times per day could be performed during a longer period of time, such as one or more weeks, one or more months, or indeed life-long treatment.

The present embodiments can therefore be used to treat a subject suffering from UTI or at least reduce the symptoms of UTI or inhibit UTI in the subject. The present embodiments can also be used to prevent UTI in a subject having a risk of suffering from UTI, such as a subject that will have a urinary catheter and/or a subject suffering from a urinary tract disorder, such as men having enlarged prostate or women with prolapse.

The subject is preferably a human subject. However, the composition of the embodiments can also be used within veterinary care to treat or prevent UTI in animals, and in particular mammals. Non-limiting examples of such mammals include horse, cow, pig, cat, dog, rabbit, guinea pig, rat and mice.

Another aspect of the embodiments relates to use of a composition comprising a pH increasing agent, a pH decreasing agent and mannose or an analogue thereof for the manufacture of a medicament for treatment, inhibition or prevention of UTI in a subject, wherein an administration pattern of the composition comprises alternately administering the pH increasing agent and the pH decreasing agent to the subject and administering the mannose or the analogue thereof to the subject.

A further aspect of the embodiments relates to a method for treatment, inhibition or prevention of UTI in a subject. The method comprises alternately administering a pH increasing agent in combination with mannose or an analogue thereof and a pH decreasing agent in combination with the mannose or the analogue thereof to the subject.

In a particular embodiment, the method comprises alternately administering a first dosage unit comprising the pH increasing agent and the mannose or the analogue thereof and a second dosage unit comprising the pH decreasing agent and the mannose or the analogue thereof to the subject.

Experimental data as presented herein show that compositions of the embodiments are capable of inducing loss of antibiotic resistance in an antibiotic-resistant bacterial strain. Thus, the antibiotic-resistant bacterial strain becomes antibiotic-susceptible or antibiotic-sensitive following exposure to the composition.

Accordingly, in an embodiment, the subject suffers from UTI caused by an antibiotic-resistant bacterial strain, preferably an antibiotic-resistant *Escherichia coli* strain.

A possible cause of this loss of antibiotic-resistance is the stress that the bacterial strain is exposed due to the alternating exposure of a basic pH and an acid pH. Thus, this loss of antibiotic-resistance in this aspect is thought to mainly be due to the alternation in pH caused by the pH increasing agent and the pH decreasing agent. This means that this unexpected feature of the composition is likely independent of the mannose or the analogue thereof.

Hence, another aspect of the embodiments relates to a method of inducing loss of antibiotic resistance in an antibiotic-resistant bacterial strain. The method comprising alternating exposing the antibiotic-resistant bacterial strain to a basic pH and an acidic pH.

In an embodiment, the method comprising alternating contacting the antibiotic-resistant bacterial strain with a pH increasing agent and a pH decreasing agent.

In an optional variant, the method also comprises contacting the antibiotic-resistant bacterial strain with mannose or an analogue thereof, such as alternating contacting the antibiotic-resistant bacterial strain with a mixture of a pH increasing agent and mannose or an analogue thereof and a mixture of a pH decreasing agent and mannose or an analogue thereof.

A further aspect of the embodiments relates to a composition comprising a pH increasing agent and a pH decreasing agent for use in inducing loss of antibiotic resistance in an antibiotic-resistant bacterial strain having infected a subject, wherein an administration pattern of the composition comprises alternately administering the pH increasing agent and the pH decreasing agent to the subject.

In an embodiment, the composition comprises the pH increasing agent, the pH decreasing agent and mannose or an analogue thereof. In such a case, the administration pattern of the composition comprises alternately administering the pH increasing agent and the pH decreasing agent to the subject and administering the mannose or the analogue thereof to the subject.

In an embodiment, the antibiotic-resistant bacterial strain is an antibiotic-resistant *Escherichia coli* strain causing urinary tract infection in the subject.

EXPERIMENTS

Example 1

Four women (between the ages of 60 and 70) with recurrent UTI (UTI 1-2 times per month) were treated according to an embodiment of the invention. Prior to the treatment, the urine of the four women was tested using bacteria test strips (NITRISTIC®, RAERAD Products, Sweden) following the instructions from the manufacturer. All women showed bacteria in the urine (strips indicating red instead of blue). The women were given a composition with 1 g calcium carbonate (pH-KALK, pH Balans AB, Sweden) together with 2 g D-mannose (DM, BECKMAN-KENKO GMBH, Germany) or 1 g citric acid (SANTA MARIA AB, Sweden) together with 2 g D-mannose (DM, BECKMAN-KENKO GMBH, Germany) and these compositions were taken in an alternating administration pattern 5 times per day (see Table 1 for details). The treatment lasted for 4 days and after completed treatment all four women displayed undetectable levels of bacteria in their urine using the same bacteria test strips as before the initiation of the treatment (strips showing blue color).

TABLE 1

| | Administration protocol | | | |
|---|---|---|---|---|
| Time of day | Day 1 | Day 2 | Day 3 | Day 4 |
| 7:00 | Used test strip to test urine prior test | | | |
| 7:30 | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water |
| 10:30 | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water |
| 13:30 | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water |
| 16:30 | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water |
| 19:30 | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water |
| 20:00 | | | | Used test strip to test urine |

Example 2

One wheelchair-bound woman (age 62), with recurrent UTI (UTI every week) was treated according to an embodiment of the invention. Prior to the treatment, the urine of the woman was tested using bacteria test strips (NITRISTIC®, RAERAD Products, Sweden) following the instructions from the manufacturer. The woman showed bacteria in the urine (strips indicating red instead of blue). The woman was given a composition with 1 g calcium carbonate (pH-KALK, pH Balans AB, Sweden) together with 2 g D-mannose (DM, BECKMAN-KENKO GMBH, Germany) or 1 g citric acid (SANTA MARIA AB, Sweden) together with 2 g D-mannose (DM, BECKMAN-KENKO GMBH, Germany). The compositions were taken in an alternating administration pattern 5 times per day (see Table 2 for details). The initial treatment lasted for 4 days. At the completion of the initial treatment the woman displayed undetectable levels of bacteria in the urine using the same bacteria test strips as before the initiation of the treatment (strips showing blue color). After the initial treatment, the woman continued with the treatment to prevent UTI according to Table 2 alternating pH three times a day for five months. The woman did not get any UTI during the five months. After discontinuing the treatment, the woman relapsed with UTI within 3 weeks.

TABLE 2

Administration protocol

| Time of day | Day 1 | Day 2 | Day 3 | Day 4 | Day 5 and five months daily |
|---|---|---|---|---|---|
| 7:00 | Used test strip to test urine prior test | | | | |
| 7:30 | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water |
| 10:30 | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | |
| 13:30 | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | 1 g citric acid + 2 g DM in ½ glass of water |
| 16:30 | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | |
| 19:30 | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water |
| 20:00 | | | | Used test strip to test urine | |

Example 3

Four women (ages 46, 56, 34, and 83) with recurrent UTI (UTI 4-6 times a year) were treated according to an embodiment of the invention. Prior to the treatment, the urine of the four women was tested using bacteria test strips (NITRISTIC®, RAERAD Products, Sweden) following the instructions from the manufacturer. All women showed bacteria in the urine (strips indicating red instead of blue). Furthermore, the urine was cultured and the lab results showed presence of $E.\ coli$ bacteria above 100000 cfu/ml (CFU=Colony Forming Units).

The women were given a composition with 1 g calcium carbonate (pH-KALK, pH Balans AB, Sweden) together with 2 g D-mannose (DM, BECKMAN-KENKO GMBH, Germany) or 1 g citric acid (SANTA MARIA AB, Sweden) together with 2 g D-mannose (DM, BECKMAN-KENKO GMBH, Germany) and these compositions were taken in an alternating administration pattern 5 times per day (see Table 3 for details). The treatment lasted for 7 days and after completed treatment all four women displayed undetectable levels of bacteria in their urine using the same bacteria test strips as before the initiation of the treatment (strips showing blue color). Furthermore, the urine was analyzed by culturing, confirming the absence of $E.\ coli$.

TABLE 3

Administration protocol

| Time of day | Day 1 | Day 2 | Day 3 | Day 4 | Day 5 | Day 6 | Day 7 | Day 8 and five months daily |
|---|---|---|---|---|---|---|---|---|
| 7:00 | Test strip to test urine prior test and urine sample sent to lab for culturing. | | | | | | | |
| 7:30 | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water |
| 10:30 | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | |
| 13:30 | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | 1 g CaCO₃ + 2 g DM in ½ glass of water |
| 16:30 | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | 1 g CaCO₃ + 2 g DM in ½ glass of water | 1 g citric acid + 2 g DM in ½ glass of water | |

TABLE 3-continued

| | | | Administration protocol | | | | | |
|---|---|---|---|---|---|---|---|---|
| Time of day | Day 1 | Day 2 | Day 3 | Day 4 | Day 5 | Day 6 | Day 7 | Day 8 and five months daily |
| 19:30 | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water |
| 20:00 | | | | | | | Test strip to test urine and urine sample sent to lab for culturing. | |

Example 4

One woman aged 35 received antibiotics (SELEXID) against UTI twice with no apparent results. The lab report showed resistant *E. coli* bacteria in the urine (above 100000 cfu/ml). Prior to the treatment, the urine was tested using bacteria test strips (NITRISTIC®, RAERAD Products, Sweden) following the instructions from the manufacturer. The test strips showed bacteria in the urine (strips indicating red instead of blue).

The woman was then treated according to an embodiment of the invention (see Table 4 for details). After 7 days of treatment the bacteria count was still higher than 100000 cfu/ml, but this time the lab report showed that the *E. coli* bacteria had become sensitive for the antibiotic. The treatment was repeated for another 7 days, after which the lab report showed less than 100000 *E. coli* cfu/ml and the woman had no symptoms of UTI. Furthermore the bacteria test strips were negative.

TABLE 4

| | | Administration protocol | | | | | |
|---|---|---|---|---|---|---|---|
| Time of day | Day 1 | Day 2 | Day 3 | Day 4 | Day 5 | Day 6 | Day 7 |
| 7:00 | Test strip to test urine prior test and urine sample sent to lab for culturing. | | | | | | |
| 7:30 | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water |
| 10:30 | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water |
| 13:30 | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water |
| 16:30 | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water |
| 19:30 | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water | 1 g citric acid + 2 g DM in ½ glass of water | 1 g $CaCO_3$ + 2 g DM in ½ glass of water |
| 20:00 | | | | | | | Test strip to test urine and urine sample sent to lab for culturing. |

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method of treating or reducing the risk of developing a urinary tract infection in a subject, comprising:
administering to a subject in need thereof a pH increasing agent, a pH decreasing agent, and mannose or an analogue thereof, wherein administering comprises an administration pattern of alternating the administration of the pH increasing agent with the administration of the pH decreasing agent to the subject, thereby treating or reducing the risk of developing a urinary tract infection in the subject wherein the pH increasing agent is administered at a dosage of about 0.1 to 20 g per day, the pH decreasing agent is administered to at a dosage of about 0.1 to 20 g per day, and the mannose and/or the analogue thereof is administered to at a dosage of about 0.1 to 50 g per day.

2. The method of claim 1, comprising:
administering, in any order, a first composition comprising the pH increasing agent, and the mannose and/or the analogue thereof; and
a second composition comprising the pH decreasing agent, and the mannose and/or the analogue thereof, wherein administering comprises an administration pattern of alternating the administration of the first composition with administration of the second composition, thereby alternating the pH of the urinary tract system of the subject and treating or reducing the risk of developing a urinary tract infection in the subject.

3. The method of claim 2, wherein the first composition comprises a first dosage unit and the second composition comprises a second dosage unit.

4. The method of claim 3, wherein the first dosage unit comprises about 0.1 to 2 g of the pH increasing agent and about 0.5 to 4 g of the mannose and/or the analogue thereof; and the second dosage unit comprises about 0.1 to 2 g of the pH decreasing agent and about 0.5 to 4 g of the mannose and/or the analogue thereof.

5. The method of claim 3, wherein the first dosage unit comprises a sachet comprising a powder mixture of the pH increasing agent and the mannose and/or the analogue thereof; the second dosage unit comprises a sachet comprising a powder mixture of the pH decreasing agent and the mannose and/or the analogue thereof; and each sachet comprises a respective number specifying an administration order according to the administration pattern.

6. The method of claim 3, wherein the first dosage unit comprises a tablet or a lozenge comprising a mixture of the pH increasing agent and the mannose and/or the analogue thereof; the second dosage unit comprises a tablet or lozenge comprising a mixture of the pH decreasing agent and the mannose and/or the analogue thereof; and each tablet or lozenge comprises a respective number specifying an administration order according to the administration pattern.

7. The method of claim 3, wherein the first dosage unit comprises a first color or pattern and the second composition comprises a second color or pattern that is different from the first color or pattern.

8. The method of claim 2, wherein the administration pattern comprises alternating administration of the first composition with administration of the second composition for a combined total of 3-7 administration times per day.

9. The method of claim 2, wherein the administration pattern comprises alternating administration of the first composition with administration of the second composition for a combined total of 5 administration times per day.

10. The method of claim 2, wherein the administration pattern comprises alternating administration of the first composition with administration of the second composition for a combined total of 3-7 administration times per day over 2-10 days.

11. The method of claim 2, wherein the administration pattern comprises alternating administration of the first composition with administration of the second composition for a combined total of 5 administration times per day over 2-10 days.

12. The method of claim 1, wherein the pH increasing agent is selected from a group consisting of a carbonate, a lactate, a hydroxide, an amine, an amide, an ammonium salt, ammonium, alanine, and pyridine, or any mixture thereof.

13. The method of claim 12, wherein the carbonate is selected from a group consisting of sodium bicarbonate, sodium carbonate, potassium bicarbonate, potassium carbonate, magnesium carbonate and calcium carbonate, or any mixture thereof.

14. The method of claim 1, wherein the pH decreasing agent is selected from a group consisting of citric acid, a straight-chain, saturated carboxylic acid, lactic acid, ascorbic acid, tartaric acid, mandelic acid, acetylsalicylic acid, benzoic acid, boric acid, ethylenediaminetetraacetic acid (EDTA), carbonic acid, maleic acid, hydrochloride, hypochlorous acid, a hypochlorite, and/or any mixture thereof.

15. The method of claim 14, wherein the straight-chain, saturated carboxylic acid is selected from a group consisting of fumaric acid, acetic acid, propionic acid, butyric acid and valeric acid, or any mixture thereof.

16. The method of claim 1, wherein the analogue of mannose is mannitol.

17. The method of claim 1, wherein the pH increasing agent is calcium carbonate, and the pH decreasing agent is lactic acid.

18. The method of claim 1, wherein the urinary tract infection is caused by an antibiotic-resistant bacterial strain.

19. The method of claim 1, wherein the urinary tract infection is caused by an antibiotic-resistant *Escherichia coli* strain.

* * * * *

UNITED STATES PATENT AND TRADEMARK OFFICE
CERTIFICATE OF CORRECTION

| | |
|---|---|
| PATENT NO. | : 10,525,069 B2 |
| APPLICATION NO. | : 15/321902 |
| DATED | : January 7, 2020 |
| INVENTOR(S) | : Constantin Raduti |

Page 1 of 1

It is certified that error appears in the above-identified patent and that said Letters Patent is hereby corrected as shown below:

On the Title Page

Item (30) Foreign Application Priority Data:
Please correct "1450829" to read -- 1450829-5 --

Signed and Sealed this
Twelfth Day of May, 2020

Andrei Iancu
*Director of the United States Patent and Trademark Office*